(12) United States Patent
Van Kruchten

(10) Patent No.: US 7,462,748 B2
(45) Date of Patent: Dec. 9, 2008

(54) PROCESS FOR THE PREPARATION OF ALKYLENE GLYCOL

(75) Inventor: Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/850,544

(22) Filed: Sep. 5, 2007

(65) Prior Publication Data

US 2008/0064881 A1 Mar. 13, 2008

(30) Foreign Application Priority Data

Sep. 7, 2006 (EP) .................... 06254655

(51) Int. Cl.
*C07C 29/10* (2006.01)

(52) U.S. Cl. ...................... 568/858; 568/867

(58) Field of Classification Search .............. 568/867; 549/230

See application file for complete search history.

(56) References Cited

U.S. PATENT DOCUMENTS

| | | | | |
|---|---|---|---|---|
| 4,117,250 | A | 9/1978 | Foster et al. | 568/858 |
| 4,283,580 | A | 8/1981 | Odanaka et al. | 568/858 |
| 4,691,041 | A | 9/1987 | Duranleau et al. | 558/277 |
| 4,982,021 | A | 1/1991 | Best et al. | 568/867 |
| 6,080,897 | A | 6/2000 | Kawabe | 568/858 |
| 6,407,279 | B1 | 6/2002 | Buchanan et al. | 558/277 |
| 6,479,715 | B1 * | 11/2002 | Strickler et al. | 568/867 |
| 2003/0013929 | A1 * | 1/2003 | Strickler et al. | 568/867 |
| 2007/0151451 | A1 | 7/2007 | Rekers et al. | 95/141 |
| 2007/0154377 | A1 | 7/2007 | Rekers | 423/245.3 |
| 2007/0197801 | A1 | 8/2007 | Bolk et al. | 549/229 |
| 2007/0197808 | A1 | 8/2007 | Bolk et al. | 549/536 |
| 2007/0203348 | A1 | 8/2007 | Bolk et al. | 549/533 |
| 2007/0203349 | A1 | 8/2007 | Bolk et al. | 549/533 |
| 2007/0203350 | A1 | 8/2007 | Bolk et al. | 549/533 |
| 2007/0203352 | A1 | 8/2007 | Bolk et al. | 549/535 |
| 2007/0203372 | A1 * | 8/2007 | Ramakers | 568/867 |
| 2007/0203379 | A1 | 8/2007 | Bolk et al. | 585/500 |
| 2007/0213545 | A1 | 9/2007 | Bolk et al. | 549/536 |
| 2008/0097129 | A1 | 4/2008 | Van Kruchten | 568/858 |
| 2008/0154051 | A1 | 6/2008 | Bolk et al. | 549/524 |
| 2008/0154052 | A1 | 6/2008 | Bolk et al. | 549/524 |

FOREIGN PATENT DOCUMENTS

| | | |
|---|---|---|
| BE | 878901 | 1/1980 |
| EP | 889025 | 1/1999 |
| EP | 889025 | 4/2002 |
| GB | 2007659 | 5/1979 |
| GB | 2049668 | 12/1980 |
| JP | 57106631 | 7/1982 |
| JP | 59013741 | 1/1984 |
| JP | 63238043 | 4/1988 |
| JP | 63238043 | 10/1988 |

OTHER PUBLICATIONS

Kirk Othmer's Encyclopedia of Chemical Technology, 4th edition, vol. 9, pp. 923-940.
Nishikubo, et al. in J. Polym. Sci., Part A: Polym. Chem., (1993) 31, 939-947.

* cited by examiner

*Primary Examiner*—Sikarl A Witherspoon

(57) ABSTRACT

A process for the preparation of an alkylene glycol, said process comprising reacting the corresponding alkylene carbonate with water in the presence of a catalyst, wherein the catalyst comprises bicarbonate as active phase, immobilized on a solid support, having one or more electropositive sites.

20 Claims, No Drawings

PROCESS FOR THE PREPARATION OF ALKYLENE GLYCOL

CROSS-REFERENCE TO RELATED APPLICATIONS

This application claims the benefit of European Patent Application No. 06254655.1, filed Sep. 7, 2006, which is incorporated herein by reference in its entirety.

FIELD OF THE INVENTION

The invention relates to a process for the preparation of an alkylene glycol by the catalytic hydrolysis of the corresponding alkylene carbonate.

BACKGROUND OF THE INVENTION

Alkylene glycols, in particular monoalkylene glycols, are of established commercial interest. For example, monoalkylene glycols are used in anti-freeze compositions, as solvents and as base materials in the production of polyalkylene terephthalates e.g. for fibers or bottles.

The production of alkylene glycols by liquid phase hydrolysis of alkylene oxide is known. The hydrolysis is generally performed by adding a large excess of water, e.g. 20 to 25 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative means for increasing the reaction selectivity without having to use a large excess of water. The hydrolysis of alkylene oxides to alkylene glycols can be performed with a smaller excess of water in a catalytic system. Therefore, these efforts have usually focused on the selection of more active hydrolysis catalysts and various catalysts have been disclosed in the literature.

In addition, processes for the production of alkylene glycols from alkylene oxides, comprising a two-step process, have been described in the art. Such processes involve the reaction of alkylene oxides with carbon dioxide in the presence of a catalyst, followed by subsequent thermal or catalytic hydrolysis of the resultant alkylene carbonate. Examples of such two-step processes include those described in JP-A-57106631, JP-A-59013741 and U.S. Pat. No. 6,080,897.

Catalysts suitable for the hydrolysis of alkylene carbonates are described in U.S. Pat. No. 4,283,580, which is directed to the use of molybdenum or tungsten in metal or compound form as catalysts in the production of substituted or unsubstituted ethylene glycols by the reaction of substituted or unsubstituted ethylene carbonates with water.

Although progress has been made in the hydrolysis of alkylene carbonates there still remains a need for a catalyst system that allows easy purification of the desired product.

SUMMARY OF THE INVENTION

We have now surprisingly found that the hydrolysis (being the catalytic conversion of alkylene carbonate with water) of alkylene carbonates to the corresponding alkylene glycol can be efficiently catalysed by a bicarbonate immobilised on a solid support. The present invention therefore provides a process for the preparation of an alkylene glycol, said process comprising reacting the corresponding alkylene carbonate with water in the presence of a catalyst, wherein the catalyst comprises bicarbonate as active phase, immobilised on a solid support, having one or more electropositive sites.

This heterogeneous system allows for facile separation of the desired product from the catalytic composition. Such separation can be accomplished without distilling of the product in the presence of the catalyst composition at the high temperatures generally required to purify alkylene glycols. A further advantage is that the concentration of catalyst is much higher with the same reactor volume. The advantage of having bicarbonate as active phase is that the only products that may leach from the catalyst are carbon dioxide and water and there are by-products or reagents of the reaction. Thus no strange molecules are part of the product stream.

DETAILED DESCRIPTION OF THE INVENTION

The alkylene carbonate used as starting material in the process of the invention has its conventional definition, i.e. a compound having a carbonate group in its molecule.

Particularly suitable are alkylene carbonates having a five-membered alkylene carbonate ring (1,3-dioxolan-2-ones) of the general formula (I),

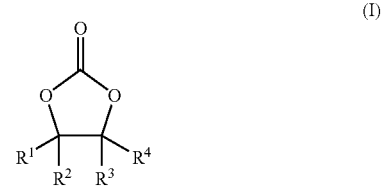

(I)

wherein $R^1$ to $R^4$ independently represent a hydrogen atom or an optionally substituted alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene carbonates therefore include ethylene carbonate, propylene carbonate, 1,2-butylene carbonate, and 2,3-butylene carbonate. In the present invention, the most preferred alkylene carbonate of the general formula (I) is ethylene carbonate, where $R^1$, $R^2$, $R^3$ and $R^4$ all represent hydrogen atoms.

Alkylene carbonate preparation is well known to the skilled person. They can be prepared by a process comprising contacting the corresponding alkylene oxide with carbon dioxide in the presence of a catalyst.

Particularly suitable are alkylene oxides of the general formula (II),

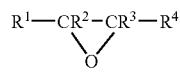

(II)

wherein $R^1$ to $R^4$ correspond to $R^1$ to $R^4$ of the corresponding alkylene carbonate. Therefore, suitable alkylene oxides include ethylene oxide, propylene oxide, 1,2-butylene oxide, and 2,3-butylene oxide. In the present invention, the most preferred alkylene oxide of the general formula (II) is ethylene oxide, where $R^1$, $R^2$, $R^3$ and $R^4$ all represent hydrogen atoms.

Alkylene oxide preparation is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, 4$^{th}$ edition, Vol. 9, pages 923-940).

The catalyst according to the present invention comprises bicarbonate as active phase, immobilised on a solid support, having one or more electropositive sites. For the activity of the catalyst it is not needed to start with the bicarbonate as active phase. It is also possible to start with a hydroxy group or with a carbonate group immobilised on the solid support. These groups are considered to be precursors for bicarbonate as active phase for this reaction. During the initial stage of the catalytic reaction the hydroxy group or the carbonate group are being converted to the bicarbonate active phase due to the presence of large amounts of $CO_2$ and water or alcohol that are formed when alkylene carbonate is being converted.

The amount of bicarbonate used in the process of the present invention is suitably in the range of from 0.0001 to 0.5 mol/mol alkylene carbonate. Preferably, the bicarbonate is present in an amount in the range of from 0.001 to 0.1 mol/mol alkylene carbonate.

The solid support is a support having one or more electropositive sites. Suitable solid supports having one or more electropositive sites include those of an inorganic nature such as carbon, silica, silica-alumina, zeolites, glass, and clays such as hydrotalcite. Such solid supports may have the cation bonded by adsorption, reaction or grafting. Further, immobilised complexing macrocycles, such as crown ethers, are also considered as solid support having one or more electropositive sites according to this invention, since these materials are able to bind a cation. Preferably, the solid support contains a quaternary ammonium, quaternary phosphonium, quaternary arsenonium, quaternary stibonium or a ternary sulfonium cation or a complexing macrocycle. More preferably, the cation is a quaternary ammonium or quaternary phosphonium ion.

Advantageously, in the present invention, solid supports comprising a strongly basic ion exchange resin are used, wherein the cation is attached to a polymeric backbone. The polymeric backbone may comprise high molecular weight polymers and co-polymers including polyalkylene, polyester, polycarbonate, polyurethane, formaldehyde resins, etc. Suitable commercially available ion exchange resins include those comprising polyacrylate or styrene-divinylbenzene copolymers as polymeric backbones. Resins with silica-based polymeric backbones, such as polysiloxanes, and resins incorporating vinylpyridine monomers in their polymeric backbones may also be used. Commercially available ion exchange resins suitable for the process of the present invention include, but are not limited to, LEWATIT 500 KR (LEWATIT is a trade mark), AMBERLITE IRA-900, AMBERLITE IRA-458 (AMBERLITE is a trade mark), AMBERJET 4200, AMBERJET 4400 (AMBERJET is a trade mark), DOWEX 1×16 (DOWEX is a trade mark), REILLEX HPQ (REILLEX is a trade mark), MARATHON-A, MARATHON-MSA (MARATHON is a trade mark) and DELOXAN AMP (DELOXAN is a trade mark). Other suitable ion exchange resins include those made according to the method described by Nishikubo, et al. in J. Polym. Sci., Part A: Polym. Chem., (1993) 31, 939-947. These resins have so-called spacer groups, comprising a chemical structure linking the polymeric backbone to the cation. Suitably, the spacer group contains an alkylene group optionally interrupted with one or more oxygen atoms.

The bicarbonate or one of its precursors hydroxyl or carbonate can be immobilised on the solid support by any technique know to the person skilled in the art. These techniques include pore volume impregnation, impregnation, precipitation and ion-exchange. Preferably, the bicarbonate or one of its precursors is immobilised on the solid support via ion-exchange. Ion exchange comprises contacting the solid support with a solution. In the preferred case of immobilising bicarbonate, the solution may comprise excess sodium-bicarbonate or it may be water saturated with $CO_2$. When the $CO_2$ saturated water solution is used, the exchange reaction is repeated until the pH of the effluent is similar to the pH of the $CO_2$-saturated solution. This step may be followed by a water wash step. Preferably, ion-exchange takes place at a temperature in the range from 0° C. to 100° C., more preferably at a range from 20° C. to 90° C. Preferably, ion-exchange takes place at atmospheric pressure.

The process of the present invention can be carried out in any reaction system suitable for a hydrolysis process.

The alkylene carbonate used in the process of the present invention may comprise purified alkylene carbonate or any other suitable alkylene carbonate. The alkylene carbonate may also be a raw product from an alkylene carbonate production unit, wherein the corresponding alkylene oxide is contacted with carbon dioxide in the presence of a catalyst. It may be that the catalyst is still present in this raw product.

Preferably, the total amount of water supplied to the reactor is an amount of at least 0.5 mol/mol alkylene carbonate, preferably at least 1 mol/mol alkylene carbonate. Preferably the total amount of water supplied to the reactor is an amount of at most 20 mol/mol alkylene carbonate, more preferably in an amount of at most 5 mol/mol alkylene carbonate, even more preferably at most 2 mol/mol alkylene carbonate.

The process of the present invention may be carried out in batch operation. However, in particular for large-scale embodiments, it is preferred to operate the process continuously.

Such continuous process can be carried out in fixed bed reactors, operated in up-flow or down-flow. Other reactor options include bubble column reactors and fluidized bed reactors.

The reactors of the present invention may be maintained under isothermal, adiabatic or hybrid conditions. Isothermal reactors are generally shell- and tube reactors, mostly of the multi-tubular type, wherein the tubes contain the catalyst and a coolant passes outside the tubes. Adiabatic reactors are not cooled, and the product stream leaving them may be cooled in a separate heat exchanger.

It may be advantageous for the process of this invention to recycle a part of the reactor output to at least one inlet of the same reactor, because any temperature difference that may arise between the top and the bottom of the reactor is minimised. Accordingly, less external temperature control is required to maintain the reaction temperature than with a conventional reactor. This is particularly advantageous when isothermal conditions are preferred. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed. The amount of reactor output mixture to be recycled may be varied to obtain optimum performance with regard to other reaction parameters employed.

A problem, which may occasionally arise in certain processes using catalysts containing the above mentioned quaternary or ternary groups, is the presence of small amounts of impurities in the product stream. For example, when strongly basic anion exchange resins, wherein the basic groups comprise quaternary ammonium or phosphonium groups, are used as the solid support for the catalytic group it has been found that during operation, small amounts of amines or phosphines tend to leach from the resin into the product stream. Other impurities in the product stream may include amines originating from corrosion inhibitors, which may be added to the water used in the process. Although the amounts of such contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odour of TMA may be detected in an amount as low as 1 ppb.

An effective measure in removing such contaminants is the use of a post-reactor bed, containing an acidic species, particularly a strongly acidic ion exchange resin, which effectively captures the contaminants. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB, and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product stream after passing it may become acidic. Using a mixture of the strongly acidic ion exchange resin in its $H^+$ form and salt form has the advantage of the pH of the product stream remaining close to neutral.

Such a post-reactor bed may be positioned after the hydrolysis reaction bed in which the process according to the present reaction is carried out. An added advantage of the strongly acidic post-reactor bed positioned after a reactor bed in which the alkylene carbonate has undergone hydrolysis to form the corresponding alkylene glycol is that any remaining alkylene carbonate, which may be still present in the product alkylene glycol product stream, is hydrolysed to alkylene glycol.

In order to allow for exhaustion and replacement or regeneration of the strongly acidic ion exchange resin during operation, it is advantageous to operate the post-reactor bed in two or more separate vessels, to allow the process to be switched between the two vessels, thus maintaining continuous operation.

Exhausted strongly acidic ion exchange resin can be regenerated by treatment with an acid, such as HCl and $H_2SO_4$. Hot sulfuric acid of 0.1 to 2 N has been proven to be effective.

In order to accommodate any swelling of the catalyst that may still occur during operation, the reactor volume can advantageously be greater than the volume occupied by the catalyst therein, preferably in the range of from 10 to 70 vol % greater.

Suitable reaction temperatures for the catalytic hydrolysis of alkylene carbonates, according to the present invention, are generally in the range of from 20 to 200° C.; temperatures in the range of from 60 to 130° C. are preferred.

The reaction pressure is usually selected in the range of from 100 to 5000 kPa, preferably in the range of from 200 to 3000 kPa, most preferably in the range of from 200 to 1500 kPa.

Having generally described the invention, a further understanding may be obtained by reference to the following examples, which are provided for purposes of illustration only and are not intended to be limiting unless otherwise specified. The following Examples will illustrate the invention.

EXAMPLES

Catalyst Preparation 150 ml of a wet ion exchange resin of the quaternary ammonium type in the chloride form (AMBERJET 4200, ex Rohm & Haas, exchange capacity 1.3 meq/ml) was slurried in a water filled glass tube. The chloride anion was exchanged by treatment with a sodium-bicarbonate solution (10 times molar excess in 2500 g of water) for approximately 5 hours (liquid hourly space velocity was 4 l/l. h). Next, the exchanged resin was washed with 1200 ml of water for approximately 2 hours (liquid hourly space velocity was 4 l/l. h). In the resulting catalyst, the chloride anions from the AMBERJET 4200 has been almost completely exchanged with the desired bicarbonate anions, the final chloride content being less than 100 ppm.

Experiment 1

The experiments were carried out in a 120 ml glass autoclave. The reactor was filled with 35 g ethylene carbonate and 21.5 g water. The hydrolysis catalyst was added in a sufficient quantity to provide 4.1 mmol of catalyst. The reactor was purged with $CO_2$ and pressurized with a $CO_2$ atmosphere of 4.5 bar (450 kpa). The reactor content was heated to 110° C., while maintaining the pressure at 4.5 bar. Samples were taken at regular time intervals of 30 minutes and analysed by gas liquid chromatography (GLC). The results are shown in table I.

TABLE I

| Catalyst | Amount (g) | Amount (mmol) | EC conversion (%; at 150 min) | MEG selectivity (%; at 100% conversion) |
|---|---|---|---|---|
| — | — | — | 13.1 | — |
| $K_2CO_3$ | 0.283 | 2.1 | 95.5 | 99.7 |
| $KHCO_3$ | 0.411 | 4.1 | 95.5 | 99.8 |
| AMBERJET 4200/$HCO_3$ | 2.75 ml | 4.1 | 54 | 99.6 |

Experiment 2

The prepared AMBERJET 4200/bicarbonate catalyst (IER capacity of 1.3 meq/ml) was tested under continuous flow conditions in a fixed-bed plug flow reactor for more than 2000 hours. The performance of the catalyst was tested in two different experiments at two liquid hourly space velocities (LHSV) of 0.51 and 0.75 l/l. h.

The catalyst performance was tested by placing 20 ml of the catalyst in a 65 cm long 0.5 inch wide Hoke tube, provided with a heating jacket using a hot oil system. An ethylene carbonate (EC)/water mixture comprising 17.5 wt % EC was pumped down-flow with an HPLC pump over the catalyst bed at a temperature of around 90° C. and a pressure of 1000 kPa for at least 2000 hours. The reaction temperature was controlled by the temperature of the hot oil system. In the centre of the catalyst bed a thermo well was placed with a thermo couple to measure the bed temperatures. The reactor effluent was cooled and collected in a product vessel, from which samples were taken for GLC analysis. The results are summarized in table II.

TABLE II

|  | Experiment 2a | Experiment 2b |
| --- | --- | --- |
| LHSV (l/l/h) | 0.51 | 0.75 |
| Temperature (° C.) | 89.7 | 88.2 |
| Selectivity (mol %) | >99.9 | >99.9 |
| Run time (hours) | Conversion (%) | Conversion (%) |
| 93.5 | 90.2 | 65.9 |
| 164.5 | 88.3 | 68.5 |
| 244.5 | 86.0 | 67.1 |
| 838.5 | 91.6 | 72.1 |
| 910.0 | 92.0 | 73.4 |
| 1005.0 | 92.4 | 72.6 |
| 1078.5 | 92.6 | 75.0 |
| 1174.5 | 89.3 | 68.9 |
| 1246.0 | 89.4 | 68.8 |
| 1342.0 | 89.5 | 68.8 |
| 1419.5 | 90.3 | 70.4 |
| 1510.0 | 90.7 | 71.6 |
| 1580.5 | 91.2 | 71.1 |
| 1702.5 | 92.1 | 70.5 |
| 1780.0 | 93.3 | 72.1 |
| 1870.5 | 91.4 | 73.8 |
| 2015.0 | 91.1 | 72.3 |
| 2111.0 | 92.2 | 73.9 |
| 2207.0 | 92.1 | 73.3 |
| 2277.0 | 92.1 | 74.8 |

The results as presented in table II clearly demonstrate that the catalyst remains active over a prolonged period of time.

What is claimed is:

1. A process for the preparation of an alkylene glycol, said process comprising reacting the corresponding alkylene carbonate with water in the presence of a catalyst, wherein the catalyst comprises bicarbonate as active phase, immobilised on a solid support, having one or more electropositive sites.

2. The process according to claim 1, wherein the solid support is a strongly basic ion exchange resin, wherein cations are attached to a polymeric backbone.

3. The process according to claim 1, wherein the solid support contains cations selected from the group consisting of quaternary ammonium, quaternary phosphonium, quaternary arsenonium, quaternary stibonium, and ternary sulfonium cations.

4. The process according to claim 2, wherein the cations are selected from the group consisting of quaternary ammonium, quaternary phosphonium, quaternary arsenonium, quaternary stibonium, and ternary sulfonium cations.

5. The process according to claim 1, wherein the solid support contains cations selected from the group consisting of quaternary ammonium cations and quaternary phosphonium cations.

6. The process according to claim 2, wherein the cations are selected from the group consisting of quaternary ammonium cations and quaternary phosphonium cations.

7. The process according to claim 1, wherein the catalyst comprises initially a carbonate group, a bicarbonate group or a hydroxyl group immobilised on the solid support.

8. The process according to claim 1, wherein the process is carried out at a temperature in the range of from 40 to 200° C. and at a pressure in the range of from 100 to 5000 kPa.

9. The process according to claim 1, wherein the alkylene carbonate is ethylene carbonate.

10. The process according to claim 1, wherein the bicarbonate is present in an amount in the range of from 0.0001 to 0.5 mol/mol alkylene carbonate.

11. The process according to claim 1, wherein the bicarbonate is present in an amount in the range of from 0.001 to 0.1 mol/mol alkylene carbonate.

12. The process according to claim 1, wherein the water is present in an amount in the range of from 0.5 to 20 mol/mol alkylene carbonate.

13. The process according to claim 1, wherein the water is present in an amount in the range of from 1 to 5 mol/mol alkylene carbonate.

14. The process according to claim 2, wherein the cations are attached to the polymeric backbone via a spacer group.

15. The process according to claim 14, wherein the spacer group comprises an alkylene group optionally interrupted with one or more oxygen atoms.

16. A process for the preparation of ethylene glycol, said process comprising reacting ethylene carbonate with water in the presence of a catalyst, wherein the catalyst comprises bicarbonate as active phase, immobilised on a solid support, wherein the solid support is a strongly basic ion exchange resin having quaternary ammonium cations are attached to a polymeric backbone.

17. The process according to claim 16, wherein the bicarbonate is present in an amount in the range of from 0.001 to 0.1 mol/mol ethylene carbonate.

18. The process according to claim 16, wherein the water is present in an amount in the range of from 1 to 5 mol/mol ethylene carbonate.

19. A process for the preparation of alkylene glycol comprising the steps of:
preparing an alkylene carbonate by contacting the corresponding alkylene oxide with carbon dioxide in the presence of a catalyst
then reacting the alkylene carbonate with water by a process according to claim 1.

20. A process for the preparation of ethylene glycol comprising the steps of:
preparing ethylene carbonate by contacting ethylene oxide with carbon dioxide in the presence of a catalyst
then reacting the ethylene carbonate with water by a process according to claim 16.

* * * * *